United States Patent [19]

Johnston

[11] 4,307,373
[45] Dec. 22, 1981

[54] SOLID STATE SENSOR ELEMENT

[75] Inventor: James S. Johnston, Bognor Regis, England

[73] Assignee: Rosemont Engineering Company Limited, Great Britain

[21] Appl. No.: 160,829

[22] Filed: Jun. 18, 1980

Related U.S. Application Data

[63] Continuation of Ser. No. 912,741, Jun. 5, 1978, abandoned.

[30] Foreign Application Priority Data

Jun. 22, 1977 [GB] United Kingdom ............... 26195/77

[51] Int. Cl.³ .............................................. H01L 7/00
[52] U.S. Cl. ..................................... 338/34; 338/309
[58] Field of Search ................... 338/34, 35; 73/27 R, 73/336.5, 362 AR, 339; 23/232 E; 200/61.04; 422/83, 88, 98; 318/483; 340/632-634

[56] References Cited

U.S. PATENT DOCUMENTS

| | | | |
|---|---|---|---|
| 2,237,006 | 4/1941 | Koller | 338/35 |
| 2,806,991 | 9/1957 | White | 338/34 X |
| 3,056,935 | 10/1962 | Jensen | 338/34 X |
| 3,479,257 | 11/1969 | Shaver | 338/34 X |
| 3,703,697 | 11/1972 | Nicholas | 338/35 |
| 3,901,067 | 8/1975 | Boardman, Jr. et al. | 338/34 X |
| 3,961,301 | 6/1976 | Fraiola | 338/35 |
| 4,013,943 | 3/1977 | Chou et al. | 338/34 X |
| 4,017,820 | 4/1977 | Ross | 338/35 |
| 4,080,564 | 3/1978 | Nitta et al. | 338/35 |

FOREIGN PATENT DOCUMENTS

| | | |
|---|---|---|
| 2540030 | 3/1976 | Fed. Rep. of Germany . |
| 2651160 | 5/1977 | Fed. Rep. of Germany . |
| 1138195 | 12/1968 | United Kingdom . |
| 1204708 | 9/1970 | United Kingdom . |
| 1374575 | 11/1974 | United Kingdom . |
| 1376769 | 12/1974 | United Kingdom . |
| 1470721 | 4/1977 | United Kingdom . |
| 1502844 | 3/1978 | United Kingdom . |
| 1518943 | 7/1978 | United Kingdom . |
| 1527406 | 10/1978 | United Kingdom . |

OTHER PUBLICATIONS

Richard C. Bridgeman, et al., IEEE Transaction on Industrial Electronics and Control Instrumentation, "Using Insulation Resistance as a Dew Point Transducer for Process Control," vol. IECI-16, No. 1, pp. 13-17, Jul. 1969.

Primary Examiner—C. L. Albritton
Attorney, Agent, or Firm—Kinney, Lange, Braddock, Westman and Fairbairn

[57] ABSTRACT

A solid state sensor element is a flat device having a film resistance thermometer on one face and a pair of spaced apart conductors on the other. The element is used for measuring selected properties of a material or the surrounding atmosphere and normally the spaced conductors are covered by a coating of a material which is electrically responsive to variations in a selected parameter of the ambient atmosphere.

17 Claims, 5 Drawing Figures

SOLID STATE SENSOR ELEMENT

This is a continuation of application Ser. No. 912,741, filed June 5, 1978, now abandoned.

This invention relates to solid state sensor elements which are responsive to or for the measurement of selected parameters of materials or of the ambient atmosphere, and is concerned more particularly with such elements for the determination of properties which vary with temperature.

A number of sensors are known for measuring, for example, the dew point, or the concentration of oxygen or other gases in an atmosphere. Examples of such sensors are described in British Pat. Nos. 1,374,575 and 1,470,721 and U.S. Pat. No. 4,013,943. Further, a proposal for a dew point transducer is described in a paper by Richard C. Bridgeman entitled "Using Insulation Resistance as a Dew Point Transducer for Process Control" in I.E.E.E. Transaction on Industrial Electronics and Control Instrumentation, July 1969. Dew point sensors using a lithium chloride solution are also known. Although these various known sensors may work well in their particular applications they are mostly rather cumbersome and relatively expensive and difficult to make reproducibly. Further, none has a basic structure which can be used for a number of different types of sensor.

According to the present invention there is provided a solid state sensor element comprising a planar substrate of electrically insulating material or a material having electrically insulating surfaces, the substrate having, on one face thereof, a first pair of electrical connection points and a temperature responsive electrically conducting path extending between them, and, on the opposite face of the substrate, a second pair of connection points and a pair of physically separate electrical conductors connected respectively to said second pair of connection points, the electrical conductors having between them an elongate gap of substantially constant width.

As will be explained hereinafter, one or more coatings of materials may be provided over the separate conductors, for the sensing of specific parameters about the ambient atmosphere for example the partial oxygen pressure or the presence of specific gases in the ambient atmosphere or for measuring humidity. In the simplest form however an uncoated device may be employed, for example for the measurement of dew point.

To measure the dew point with a device of the type described above, means may be provided responsive to the electrical resistance between the separate electrical conductors and the temperature responsive conductive path may be connected to a measuring circuit for determining the temperature of the device. Then, the device may be cooled with the cooling continuing until there is a decrease in resistance between said conductors caused by the condensation of moisture on the surface of the device. The temperature at which this change in resistance occurs is a measure of the dew point. The cooling may conveniently be effected by attaching the substrate to a Peltier device. Instead of having the conductors uncoated, they may be coated with a thin layer of dielectric material, e.g. glass, and the change in capacitance between the two conductors rather than the change of conductance can be sensed to determine when the dew point has been reached.

In another embodiment of the invention, the conductors are coated with a layer of refractory oxide material of the kind which has an electrical conductivity dependent on the presence and/or concentration of a gas or gases in the ambient atmosphere. For example the electrical conductivity of certain refractory oxides are dependent on the partial pressure of oxygen in their immediate vicinity. A typical example of such an oxide is zirconia doped with yttria and thus a layer of this material may be coated over the conductors. The resistance between the two conductors is a measure of the partial pressure of the oxygen but is temperature-dependent. The temperature responsive conductive path may be used not only for measuring the temperature but can also be used for heating the device. For example the current through this temperature responsive conductive path might be controlled so that the device is held at a predetermined temperature in the range of say 400° C. to 800° C.

Instead of zirconia doped with yttria, any of the following oxides may be used:

| Simple oxides | | Complex oxides |
| --- | --- | --- |
| Cobalt oxide | $Co_3O_4$ | Bismuth molybdenum oxide |
| Nickel oxide | $NiO$ | Vanadium molybdenum oxide |
| Copper oxide | $CuO$ | Uranium antimony oxide |
| Chromium oxide | $Cr_2O_3$ | Strontium iron oxide |
| Uranium oxide | $UO_2$ | |

As another example of the use of a coating over the conductors to sense or measure the concentration of a gas, a semi-conductor coating may be applied over these conductors; such a coating shows the variations in resistance which is dependent on the concentration of certain toxic gases such as hydrogen sulphide and carbon monoxide. Again the resistance depends on the temperature of the device but the temperature responsive conductive path on the reverse side enables the temperature to be measured and controlled by adjusting the current flowing in this path until its resistance reaches the value corresponding to the desired temperature. The semi-conductor coating may be zinc oxide.

As yet another example of the use of a device with a coating over the conductors, these conductors may be coated with a porous material. For measuring relative humidity, a porous material such as aluminum oxide may be used which is allowed to absorb moisture from the atmosphere. Such moisture will change the conductivity and the dielectric constant and hence measurement may be made either of the resistance or the capacitance between the conductors. To determine the relative humidity it is necessary to know the temperature of the ambient atmosphere and this may be measured using the temperature responsive conductive path on the device.

The dew point may be determined by coating the conductors with a porous material which is impregnated with a solution of a hygroscopic material, preferably lithium chloride. With this device, an alternating current may be passed between the two conductors so raising the temperature of the device and causing the solution of hygroscopic material to evaporate. The evaporation will reduce the conductivity so reducing the heating effect and hence the device will reach a stable temperature. This temperature corresponds to that at which the vapour pressure over the lithium chloride solution is an equilibrium with that of the surrounding atmosphere. The temperature can be determined from the temperature responsive conductive path on the device and this can be related to the dew point of the surrounding atmosphere. An alternative method of operating this device is to pass an adjustable current through the temperature responsive conductive path so causing it to heat up until a desired conductivity is sensed between the two conductors. Measurement of the resistance of the temperature responsive conductive path enables the temperature of the device to be determined. Conveniently an electronic circuit is employed for this purpose to determine the ratio of the voltage drop across this path to the current flowing through it.

The dew point may also be measured by the above process but with the conductors coated with a mixture of a hygroscopic material and a gelling agent. In one example the coating is provided by painting the conductors with a solution containing 2 grams lithium chloride and 4 grams polyvinyl alcohol made up to 100 ml with water.

The present invention will now be further described, by way of example only, with reference to the accompanying drawings, in which.

Referring to FIG. 1 there is shown at (a) one face of an elongate thin substrate 10 of electrically insulating material on which is printed a temperature responsive conductive path 11 extending between two regions 12, 13 to which are connected leads 14, 15. The substrate 10 is conveniently a plate of ceramic material, such as alumina. The path is preferably formed of platinum although it is possible to use other metals such as nickel or copper or their alloys in resistance thermometer devices. Preferably the path is formed of a fused vitreous material containing platinum particles in the way known for the formation of resistance thermometers. An insulating protective coating such as a glazed coating may be provided over this path.

Figure 1A:
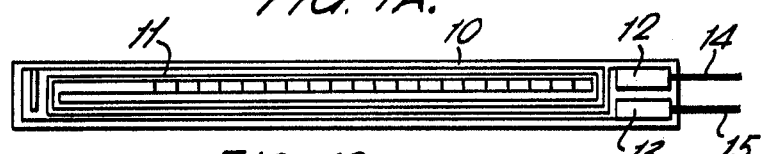
FIGS. 1A and 1B illustrate respectively the two faces of one embodiment of a sensor element constructed in accordance with the present invention.
Figure 1B:
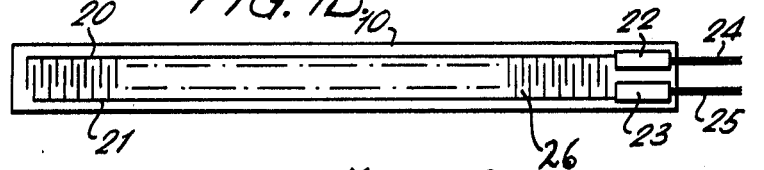

In FIG. 1B the other face of the device of FIG. 1A is shown. This face has interdigitated conductors 20,21 forming a grid and connected respectively to terminal areas 22, 23 to which are connected leads 24, 25 respectively. These conductors 20, 21 are conveniently formed of a noble metal such as gold printed in the known way on the substrate 10. Over the conductors 20, 21 there may be a coating of any of the forms described previously for example of refractory oxides such as zirconia doped with yttria or of porous material such as aluminium oxide or of a semiconductor depending on the required use of the device. As can be seen in FIG. 1B, the conductors 20 and 21 are physically separate and have between them an elongate gap 26 which has a serpentine shape and is of substantially constant width.

Figure 2A:
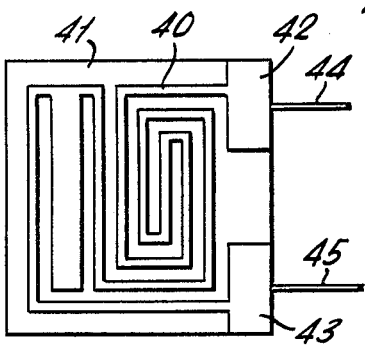
FIGS. 2A and 2B illustrate respectively the two faces of a second embodiment of the invention.
Figure 2B:
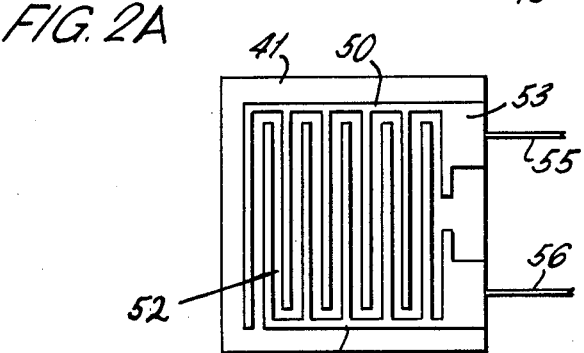

A second embodiment is shown in FIGS. 2A and 2B. At FIG. 2A there is shown a resistance thermometer comprising a conductive path 40 printed on one side of a thin plate 41 of electrically insulating material, e.g. on ceramic, constituting the substrate of the device. The two ends of the resistance thermometer path 40 are connected respectively to conductive regions 42, 43 forming terminals for the connection of lead-out conductors 44, 45. This path 40 may be formed of any suitable temperature responsive material as described above and is preferably formed of platinum particles embodied in a vitreous coating.

As shown at FIG. 2B, the other side of the substrate 41 has two conductors 50, 51 forming an interdigitated array, these two conductors being formed integrally with terminal areas 53, 54 which are connected to output leads 55, 56. These conductors 50, 51 are conveniently of gold and may be printed on the substrate in the known way. The face of the device shown in FIG. 2B may be coated in any of the manners previously described depending on the required use of the device, the coating extending over the two conductors 50, 51. Again, the conductors 50 and 51 are separated by an elongate gap 52 of substantially uniform width.

The thickness of the substrate is not critical so long as the two surfaces can be assumed to be at the same temperature. The substrate would usually be a thin plate, the thickness being small compared with its other dimensions.

Figure 3:
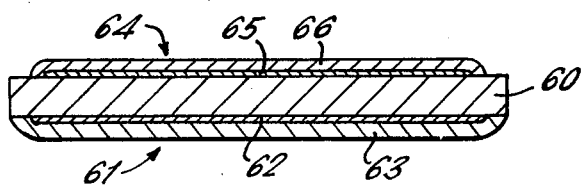
FIG. 3 is a cross-sectional view through an example of the invention.

FIG. 3 is a cross-sectional view taken through a typical sensor element and shows the disposition on a substrate 60 of, on one face 61 thereof, a temperature responsive conducting path 62 covered by a protective impervious glass coating 63, and, on the other face 64 thereof, conductors 65 and a coating 66, if any.

In one particular example of the invention, a humidity sensor has the form as shown in FIGS. 1A and 1B, comprising an alumina substrate with a vitreous platinum resistance thermometer path and gold interdigitated conductors. A coating is provided over the interdigitated grid by painting the entire face of the element with a solution of 2 g lithium chloride and 4 g polyvinyl alcohol made up to 100 ml with water. The sensor is about 3 mm wide, 30 mm long and 0.6 mm thick. The leads are of 0.3 mm diameter platinum wire. The resistance thermometer path has an ice-point resistance of $100\Omega \pm 0.1\Omega$ and a temperature coefficient of resistance ($\alpha$) of $0.00385°$ $C.^{-1}$.

In another example, an oxygen sensor has the form as shown in FIGS. 2A and 2B comprising an alumina substrate with a vitreous platinum resistance thermometer path and gold interdigitated conductors. The entire face having the interdigitated array is coated with yttria doped zirconia, which is made adherent by mixing in powder form with between 10 and 30%, and preferably 20% by volume of sodium silicate.

The sensor is about 3 mm square and 0.6 mm thick with platinum wire leads of 0.1 mm diameter. The resistance thermometer path has an ice-point resistance of $10\Omega \pm 0.1\Omega$ and a temperature coefficient of resistance ($\alpha$) of $0.00385°$ $C.^{-1}$.

The separate conductors on the face of the sensor device opposite the temperature responsive path may take other forms besides the interdigitated arrangement described in the examples. In the simplest arrangement the conductors may be two parallel paths.

Instead of a metallic path having a positive temperature coefficient of resistance, the temperature reponsive path of the element may be formed of a thermistor material.

Also, the lead outs from the two faces of the element may extend from the same end or edge thereof, or alternatively may extend from opposite ends or edges, in which case they may be used for mechanically supporting the element.

The device illustrated in FIGS. 2A and 2B may conveniently be mounted in a T05 transistor can with the top of the can perforated so that the element is exposed to ambient gases.

I claim:

1. A solid state sensor element comprising a planar substrate of a material selected from the group consisting of electrically insulating material and material having electrically insulating faces, the substrate having, on one face thereof, a first pair of electrical connection points and a temperature responsive electrically conducting path extending between forming a resistance thermometer element, and, on the opposite face of the substrate, a second pair of connection points and a pair of physically separate electrical conductors connected respectively to said second pair of connection points, the electrical conductors having between them an elongate gap of substantially constant width.

2. A sensor element as claimed in claim 1, including at least one coating over said pair of conductors, the coating being of a material which is electrically responsive to variations in a selected parameter of the ambient atmosphere.

3. A sensor element as claimed in claim 2, wherein the coating is a layer of a refractory oxide material having an electrical conductivity which is dependent on the presence of a gas or gases in the ambient atmosphere.

4. A sensor element as claimed in claim 3, wherein refractory oxide layer is of zirconia doped with one of the materials from the group consisting of yttria, and the following oxides:

| Simple oxides | | Complex oxides |
| --- | --- | --- |
| Cobalt oxide | $Co_3O_4$ | Bismuth molybdenum oxide |
| Nickel oxide | $Ni\,O$ | Vanadium molybdenum oxide |
| Copper oxide | $Cu\,O$ | Uranium antimony oxide |
| Chromium oxide | $Cr_2O_3$ | Strontium iron oxide |
| Uranium oxide | $U\,O_2$ | |

5. A sensor element as claimed in claim 4, wherein the layer includes between 10 and 30% by volume of sodium silicate.

6. A sensor element as claimed in claim 2, wherein the coating is of a semi-conductor material.

7. A sensor element as claimed in claim 6, wherein the semi-conductor material is zinc oxide.

8. A sensor element as claimed in claim 2, wherein the coating is of a porous material.

9. A sensor element as claimed in claim 8, wherein the porous material is aluminum oxide.

10. A sensor element as claimed in claim 8, wherein the porous material is impregnated with a solution of a hygroscopic material.

11. A sensor element as claimed in claim 10, wherein the hygroscopic material is lithium chloride.

12. A sensor element as claimed in claim 2, wherein the coating is a mixture of a hygroscopic material and a gelling agent.

13. A sensor element as claimed in claim 12, wherein the coating is a mixture of lithium chloride and polyvinyl alcohol.

14. A sensor element as claimed in claim 1, wherein the temperature responsive electrically conducting path has an impervious coating of an inert material.

15. A sensor element as claimed in claim 1, wherein the temperature responsive electronically conducting path is formed of a fused vitreous film containing platinum particles.

16. A sensor element as claimed in claim 1 wherein said electrical conductors are films of noble metal.

17. A sensor element as claimed in claim 1, wherein said electrical conductors are interdigitated one with the other.

* * * * *